United States Patent
Suh et al.

(10) Patent No.: US 9,884,315 B2
(45) Date of Patent: Feb. 6, 2018

(54) COMPOSITE OXIDE CATALYST FOR PREPARING BUTADIENE AND METHOD OF PREPARING THE SAME

(71) Applicant: LG CHEM, LTD., Seoul (KR)

(72) Inventors: Myung Ji Suh, Daejeon (KR); Kyong Yong Cha, Daejeon (KR); Dae Heung Choi, Daejeon (KR); Ye Seul Hwang, Daejeon (KR); Dong Hyun Ko, Daejeon (KR)

(73) Assignee: LG CHEM, LTD., Seoul (KR)

(*) Notice: Subject to any disclaimer, the term of this patent is extended or adjusted under 35 U.S.C. 154(b) by 98 days.

(21) Appl. No.: 14/906,426

(22) PCT Filed: Aug. 24, 2015

(86) PCT No.: PCT/KR2015/008833
§ 371 (c)(1),
(2) Date: Jan. 20, 2016

(87) PCT Pub. No.: WO2016/088985
PCT Pub. Date: Jun. 9, 2016

(65) Prior Publication Data
US 2017/0232426 A1 Aug. 17, 2017

(30) Foreign Application Priority Data

Dec. 5, 2014 (KR) .................. 10-2014-0173967

(51) Int. Cl.
| | |
|---|---|
| *B01J 27/192* | (2006.01) |
| *B01J 37/00* | (2006.01) |
| *B01J 37/04* | (2006.01) |
| *B01J 37/08* | (2006.01) |
| *C07C 5/48* | (2006.01) |

(52) U.S. Cl.
CPC ......... *B01J 27/192* (2013.01); *B01J 37/0009* (2013.01); *B01J 37/04* (2013.01); *B01J 37/08* (2013.01); *C07C 5/48* (2013.01); *C07C 2527/192* (2013.01)

(58) Field of Classification Search
CPC ...... B01J 27/192; B01J 37/0009; B01J 37/04; B01J 37/08
USPC .............. 502/212, 305–307, 316–319, 321
See application file for complete search history.

(56) References Cited

U.S. PATENT DOCUMENTS

| | | | |
|---|---|---|---|
| 3,320,331 A | 5/1967 | Gaspar | |
| 3,642,930 A | 2/1972 | Grasselli et al. | |
| 4,176,234 A * | 11/1979 | Grasselli ............. | B01J 23/8876 502/212 |
| 4,182,907 A * | 1/1980 | Grasselli ............. | B01J 23/8876 562/546 |
| 4,483,997 A | 11/1984 | McEntire et al. | |
| 4,732,884 A * | 3/1988 | Sarumaru ............. | B01J 23/002 502/205 |
| 5,212,137 A * | 5/1993 | Suresh ................. | B01J 23/8872 502/212 |
| 9,399,606 B2 * | 7/2016 | Ruttinger .................. | C07C 5/48 |
| 2013/0281748 A1 | 10/2013 | Cha et al. | |
| 2015/0151292 A1 * | 6/2015 | Suh ...................... | B01J 29/0341 585/626 |
| 2015/0352534 A1 * | 12/2015 | Kim ...................... | B01J 27/236 502/176 |
| 2016/0256855 A1 * | 9/2016 | Choi ...................... | B01J 29/076 |

FOREIGN PATENT DOCUMENTS

| | | | | |
|---|---|---|---|---|
| CN | 103298771 A | 9/2013 | | |
| JP | 2008088140 A | 4/2008 | | |
| KR | 10-2010-0042935 A | 4/2010 | | |
| KR | 10-1303403 | * | 9/2013 | ............... B01J 8/04 |
| KR | 10-1303403 B1 | 9/2013 | | |
| KR | 10-2014-0119222 A | 10/2014 | | |

OTHER PUBLICATIONS

"Studies on Oxidative Dehydrogenation of n-Butane on Bismuth Molybdate-Aluminium Phosphate Catalysts. I. Catalyst Characterisation" Shenoy, et al.; J.Chem. Tech. Biotechnol, 1986, 36, 95-109.
"Effects of Bi on the Catalytic Performance of MoVO/AlPO4 Catalyst for Selective Oxidation of Isobutene", Xitao Wang, et al., Chinese Journal of Catalysis, vol. 32, No. 2, pp. 352-356 (2011).
Shenoy et al. "Studies on Oxidative Dehydrogenation of n-Butane on Bismuth Molybdate-Aluminium Phosphate Catalysts. I. Catalyst Characterisation," J. Chem. Tech. Biotechnol., 36: 95-109, (1986).

* cited by examiner

*Primary Examiner* — Patricia L. Hailey
(74) *Attorney, Agent, or Firm* — Dentons US LLP

(57) ABSTRACT

Disclosed are a composite oxide catalyst for preparing butadiene and a method of preparing the same. More particularly, a composite oxide catalyst, for preparing butadiene, including a metal composite oxide and AlPO$_4$, and a method of preparing the same are disclosed.

According to the present disclosure, a composite oxide catalyst for preparing butadiene, which includes a specific binder material, prevents generation of ingredients with a high boiling point, has superior catalyst strength, catalytic activity and butadiene yield, and a method of preparing the same are provided.

6 Claims, No Drawings

COMPOSITE OXIDE CATALYST FOR PREPARING BUTADIENE AND METHOD OF PREPARING THE SAME

This application is a National Stage Entry of International Application No. PCT/KR2015/008833, filed Aug. 24, 2015, and claims the benefit of Korean Application No. 10-2014-0173967 filed on Dec. 5, 2014, all of which are hereby incorporated by reference in their entirety for all purposes as if fully set forth herein.

TECHNICAL FIELD

The present disclosure relates to a composite oxide catalyst for preparing butadiene and a method of preparing the same. More particularly, the present disclosure relates to a composite oxide catalyst for preparing butadiene, which includes a specific binder material, prevents generation of ingredients with a high boiling point, has superior catalyst strength, catalytic activity and butadiene yield, and a method of preparing the same.

BACKGROUND ART

Demand for 1,3-butadiene as an intermediate product of petrochemicals and value thereof are gradually increasing.

As methods of preparing 1,3-butadiene, there are naphtha cracking, direct butene dehydrogenation, oxidative butene dehydrogenation, etc.

Thereamong, oxidative butene dehydrogenation means a reaction in which 1,3-butadiene and water are generated through reaction of butene and oxygen in the presence of a metal oxide catalyst. Through this reaction, stable water is generated and thus this reaction is very advantageous from a thermodynamic point of view.

In addition, since the reaction is an exothermic reaction unlike direct butene dehydrogenation, 1,3-butadiene can be obtained in a high yield even at a low reaction temperature, compared to the direct dehydrogenation. Further, since the oxidative butene dehydrogenation does not require additional heat supply, it is very suitable as a commercially used process.

However, since the metal oxide catalyst should have catalytic activity and durability even under high temperature and pressure of oxidative dehydrogenation, loss of active material exhibiting catalytic activity should be minimized and high mechanical strength is required.

In general, so as to increase mechanical strength of metal oxide catalysts, a binder such as silica along with a metal oxide catalyst precursor is added during catalyst-molding. However, such a method has a limitation in increasing mechanical strength of metal oxide catalysts. In addition, metal oxide catalysts prepared through such a method reduce performance of catalysts or cause unnecessary side reaction depending upon characteristics of reactions.

RELATED DOCUMENTS (Patent Document 1) Korean Patent Laid-Open Publication No. 2014-0119222 (10 Oct. 2014)

DISCLOSURE

Technical Problem

Therefore, the present invention has been made in view of the above problems, and it is one object of the present invention to provide a composite oxide catalyst for preparing butadiene, which includes a specific binder material, prevents generation of ingredients with a high boiling point, has superior catalyst strength, catalytic activity and butadiene yield, and a method of preparing the same.

The above and other objects can be accomplished by the present invention described below.

Technical Solution

In accordance with one aspect of the present invention, provided is a composite oxide catalyst for preparing butadiene, comprising a metal composite oxide and $AlPO_4$.

In accordance with another aspect of the present invention, provided is a composite oxide catalyst for preparing butadiene, comprising a metal composite oxide and a binder, wherein the binder is $AlPO_4$.

In accordance with yet another aspect of the present invention, provided is a method of preparing a metal composite oxide catalyst for preparing butadiene, the method comprising: extrusion molding in a pellet by mixing a metal composite oxide precursor powder and $AlPO_4$; and firing the pellet.

Advantageous Effects

As apparent from the fore-going, the present invention advantageously provides a composite oxide catalyst for preparing butadiene, which includes a specific binder material, prevents generation of ingredients with a high boiling point, has superior catalyst strength, catalytic activity and butadiene yield, and a method of preparing the same.

Best Mode

Hereinafter, the present disclosure is described in detail.

The present inventors confirmed that, when $AlPO_4$ is added during preparation of a composite oxide catalyst for preparing butadiene, enhanced strength and catalytic activity are exhibited, compared to the case that the existing binder such as silica is added. Based on this, the present inventors completed the present disclosure based on this.

The composite oxide catalyst for preparing butadiene according to the present disclosure includes a metal composite oxide and $AlPO_4$.

In another embodiment, the composite oxide catalyst for preparing butadiene according to the present disclosure includes a metal composite oxide and a binder. Here, the binder may be $AlPO_4$.

In an embodiment, the binder may be included in an amount of 5 to 30% by weight, 5 to 15% by weight, or 5 to 10% by weight based on 100% by weight of the composite oxide catalyst. Within this range, the catalyst exhibits superior mechanical strength, butene transition rate, and butadiene selectivity and yield.

In an embodiment, the metal composite oxide may be a compound represented by Formula 1 below:

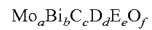   [Formula 1]

wherein C is one or more of trivalent cationic metals, D is one or more divalent cationic metals, E is one or more of monovalent cationic metals, and, when a is 12, b is 0.01 to 2, c is 0.001 to 2, d is 5 to 12, e is 0 to 1.5, and f is determined to adjust a valence with other ingredients.

The trivalent cationic metal may be, for example, one or more selected from the group consisting of Al, Ga, In, Ti, Fe, La, Cr and Ce.

The divalent cationic metal may be, for example, one or more selected from the group consisting of Be, Mg, Ca, Sr, Ba, Ra, Co, Zn and Cu.

The monovalent cationic metal may be, for example, one or more selected from the group consisting of Li, Na, K, Rb, Cs, Ag and Fr.

In another embodiment, the metal composite oxide may be a molybdate-bismuth based composite oxide.

The molybdate-bismuth based composite oxide is not specifically limited so long as may be used in general oxidative butene dehydrogenation.

In an embodiment, the molybdate-bismuth based composite oxide may be a metal composite oxide including molybdenum, bismuth, and cobalt.

In an embodiment, through oxidative dehydrogenation of the present disclosure, butadiene may be prepared by reacting raw material gas including N-butene and gas including molecular oxygen in the presence of a catalyst.

A reactor used in the oxidative dehydrogenation is not specifically limited so long as generally used in the art. In an embodiment, a tubular reactor, a tank reactor, a fluidized-bed reactor, or a fixed bed reactor may be used.

In an embodiment, the fixed bed reactor may be a multitubular reactor or a plate-type reactor.

In an embodiment, the reactor may be installed inside an electric furnace to constantly maintain reaction temperature of a catalyst layer and allow oxidative dehydrogenation to be performed when a reactant continuously passes through a catalyst layer.

In the composite oxide catalyst for preparing butadiene, a mole ratio of Mo metal to Al metal may be 12:0.5 to 3, 12:0.5 to 1.5, or 12:0.8 to 1.2. Within this range, the catalyst exhibits superior mechanical strength, butene transition rate, and butadiene selectivity and yield.

With regard to the acidity of the composite oxide catalyst for preparing butadiene, ratios of acid sites may be respectively 10 to 30%, 20 to 50%, and 40 to 60%, based on ammonia desorption temperatures of 150° C., 580° C., and 720° C. Within these ranges, overall catalyst characteristics are enhanced.

The acidity of the present disclosure is calculated by measuring an ammonia desorption amount according to temperature elevation through analysis of temperature-programmed desorption of ammonia ($NH_3$-TPD) per 0.15 g of the catalyst, and then separating spectra using Fourier transform spectroscopy to calculate a relative area ratio. In general, acidity is considered to be low as ammonia desorption is carried out at low temperature.

In an embodiment, the strength of the composite oxide catalyst for preparing butadiene may be 6.0 kgf or more, 6.0 to 8.0 kgf, or 6.0 to 7.0 kgf. Within this range, the catalyst exhibits superior mechanical properties and balanced activity.

The strength of the present disclosure indicates the highest pressure among pressures applied by slowly adding pressure by means of a circular tip with a diameter of 10 mm of a digital forcegauge (SLD 50 FGN) manufactured by SPC technology.

A method of preparing the metal composite oxide catalyst for preparing butadiene includes extrusion molding in a pellet by mixing a metal composite oxide precursor powder and $AlPO_4$; and firing the pellet.

In another embodiment, the method of preparing the metal composite oxide catalyst for preparing butadiene may include mixing a metal composite oxide precursor powder, a binder, and silica gel and extrusion-molding the same in a pellet; drying the extrusion-molded pellet; and firing the dried pellet.

A method, device, and condition of the extrusion molding are not specifically limited so long as used in preparing general metal composite oxide catalysts for preparing butadiene.

Methods, devices, and conditions of the drying and the firing are not specifically limited so long as used in preparing general metal composite oxide catalysts for preparing butadiene.

In an embodiment, the drying may be carried out at 90 to 200° C. or 110 to 150° C. for 5 to 100 hours or 10 to 30 hours.

In an embodiment, the firing may be carried out at 400 to 600° C., 400 to 500° C., or 450 to 500° C.

Descriptions for the metal composite oxide are the same as those for the metal composite oxide catalyst for preparing butadiene according to the present disclosure described above.

In an embodiment, the metal composite oxide precursor powder may be prepared through a co-precipitation step, an aging step, and a drying step.

In another embodiment, the metal composite oxide precursor powder may be prepared through a) a step of preparing a first solution including a bismuth precursor; a monovalent, divalent, or trivalent cationic metal precursor; a potassium precursor; and a cesium precursor; b) a step of preparing a second solution by dissolving a molybdenum precursor therein; c) a step of mixing the first solution and the second solution; d) a step of reacting the mixed solution; and e) a step of drying a product generated through the reaction.

In an embodiment, the step (c) may be a step in which the first solution is added to the second solution, followed by mixing.

In another embodiment, the metal composite oxide precursor powder may be prepared through i) a step of preparing a first solution including a monovalent, divalent, or trivalent cationic metal precursor, a potassium precursor, and a cesium precursor; ii) a step of preparing a second solution including a bismuth precursor dissolved therein; iii) a step of preparing a third solution including a molybdenum precursor dissolved therein; iv) a step of preparing a first mixture prepared by mixing the first solution and the second solution; v) a step of preparing a second mixture by mixing the first mixture and the second solution; vi) a step of reacting the second mixture; and vii) a step of drying a product prepared through the reaction.

Sequences of the steps (i) to (iii) steps are not specifically limited.

In an embodiment, a metal ingredient including the monovalent, divalent or trivalent cation may be one or more selected from the group consisting of cobalt, zinc, magnesium, manganese, nickel, copper, iron, rubidium, sodium, aluminum, vanadium, zirconium, and tungsten.

In another embodiment, the metal ingredient including the monovalent, divalent or trivalent cation may be one or more selected from cobalt, manganese, nickel, and iron.

A metal precursor used in preparing the metal composite oxide precursor powder is not specifically limited and may be any one generally used in the art.

In an embodiment, the metal precursor may be a metal salt including a corresponding metal ingredient. The corresponding metal ingredient may be, for example, a nitrate or an ammonium salt.

In another embodiment, bismuth nitrate (III) may be used as a bismuth precursor, and ammonium molybdate may be used as a molybdenum precursor.

In an embodiment, since the bismuth nitrate is not easily dissolved in water, the bismuth nitrate may be dissolved after adding acid to the water. Here, the acid is added in an amount in which bismuth may be completely dissolved.

In an embodiment, the acid may be an inorganic acid. In another embodiment, the acid may be nitric acid.

In the step of reacting the second mixture, reaction temperature may be, for example, room temperature to 80° C. or 50 to 70° C., and reaction time may be, for example, 5 minutes to 24 hours or 10 minutes to 4 hours.

Now, the present invention will be described in more detail with reference to the following examples. These examples are provided only for illustration of the present invention and should not be construed as limiting the scope and spirit of the present invention.

EXAMPLES

Example 1

<Preparation of Metal Composite Oxide Catalyst Precursor>

100 g of iron nitrate 9-hydrate ($Fe(NO_3)_3 \cdot 9H_2O$), 300 g of cobalt nitrate 6-hydrate ($Co(NO_3)_2 \cdot 6H_2O$), and 4 g of cesium nitrate ($CsNO_3$) were dissolved in distilled water and stirred. Separately, 100 g of bismuth nitrate 5-hydrate ($Bi(NO_3)_2 \cdot 5H_2O$) was added to distilled water including nitric acid and dissolved therein while stirring. After confirming that bismuth was completely dissolved, a bismuth solution was added to a solution including a precursor of cobalt, iron and cesium dissolved therein to prepare an acidic solution including precursors of a precursor of cobalt, iron, cesium and bismuth dissolved therein. In addition, 432 g of ammonium molybdate 4-hydrate (($NH_4)_6$ ($MO_7O_{24}) \cdot 4H_2O$) was separately dissolved in distilled water and stirred. The prepared acidic solution including the cobalt, iron, cesium, and bismuth precursors dissolved therein was added dropwise to the prepared aqueous molybdate solution. Here, a mole ratio of the metal ingredients was as follows. Mo:Bi:Fe:Co:Cs=12:1:1.2:5:0.1.

A mixture prepared by mixing as described above was stirred at room temperature for one hour by means of a magnetic stirrer to generate a precipitate. The precipitate was dried for 16 hours or more in a 120° C. convection oven and comminuted. As a result, a powder-type metal composite oxide catalyst precursor with a particle diameter of 355 μm or less was obtained.

<Extrusion Molding>

Water and alcohol, which were mixed in equal amount, were added to 90 parts by weight of the obtained metal composite oxide catalyst precursor powder and 10 parts by weight of $AlPO_4$, followed by kneading until a water content was about 15% by weight. Resultant dough was fed to an extruder constituted of an electric motor, an outer body, a screw-type internal rotor, and a front die. The dough was extruded and, at the same time, cut by a rotating cutter, while being passing through a die having a circular hole with a size of 6 mm. As a result, a pellet-type extrusion molding catalyst having a diameter of 6 mm and a length of 6 mm was prepared.

<Drying and Firing>

The prepared extrusion molding catalyst was dried in a 90° C. oven for two to five hours, followed by firing in a 430 to 480° C. electric furnace for five hours while elevating temperature at a rate of 1° C./min. Finally, a metal composite oxide catalyst including Mo and Al in a ratio of 12 to 1 was prepared.

Example 2

A metal composite oxide catalyst was prepared in the same manner as in Example 1, except that a mole ratio of Fe as a metal ingredient was determined to satisfy the following mole ratio of metal ingredients: Mo:Bi:Fe:Co:Cs=12:1:1.3:5:0.1 (Mo:Al=12:1).

Example 3

A metal composite oxide catalyst was prepared in the same manner as in Example 1, except that $AlPO_4$ was added in an amount of 5 parts by weight to satisfy the following mole ratio of metal ingredients: Mo: Bi:Fe:Co:Cs=12:1:1.2:5:0.1.

Example 4

A metal composite oxide catalyst was prepared in the same manner as in Example 1, except that $AlPO_4$ was added in an amount of 30 parts by weight to satisfy the following mole ratio of metal ingredients: Mo:Bi:Fe:Co:Cs=12:1:1.2:5:0.1.

Comparative Example 1

A metal composite oxide catalyst was prepared in the same manner as in Example 1, except that $AlPO_4$ was not used and silica was added in an amount of 3 parts by weight to satisfy the following ratio: Mo:Si=12:3.

Comparative Example 2

A metal composite oxide catalyst was prepared in the same manner as in Example 1, except that $AlPO_4$ was not used.

Comparative Example 3

A metal composite oxide catalyst was prepared in the same manner as in Example 1, except that 110 g of iron nitrate 9-hydrate ($Fe(NO_3)_3 \cdot 9H_2O$) was used such that a mole ratio of metal ingredients included in a mixture was Mo:Bi:Fe:Co:Cs=12:1:1.3:5:0.1, $AlPO_4$ was not used, and silica was used in an amount of 1 part by weight such that a ratio of Mo to Si was 2:1.

The strengths of the metal composite oxide catalysts prepared according to Examples 1 to 4 and Comparative Examples 1 to 3 were determined as the highest force when pressure was slowly applied by means of a circular tip with a diameter of 10 mm of a digital force gauge (SLD 50 FGN) manufactured by SPC technology. Results are summarized in Table 1 below.

TABLE 1

| Classification | Example 1 | Example 2 | Example 3 | Example 4 | Comparative Example 1 | Comparative Example 2 | Comparative Example 3 |
|---|---|---|---|---|---|---|---|
| Binder | AlPO$_4$ | AlPO$_4$ | AlPO$_4$ | AlPO$_4$ | Silica | — | Silica |
| Fed amount (mol) | Mo:Al = 12:1 | Mo:Al = 12:1 | Mo:Al = 12:0.5 | Mo:Al = 12:3 | Mo:Si = 12:3 | Mo:Si = 12:0 | Mo:Si = 12:1 |
| Catalyst strength (kgf) | 6.46 | 6.79 | 6.12 | 7.09 | 5.55 | 1.89 | 2.82 |

TEST EXAMPLE

Butadiene was prepared using the metal composite oxide catalyst prepared according to each of Examples 1 to 4 and Comparative Examples 1 to 3. Results are summarized in Table 2 below.

1-Butene and oxygen were used as reactants and, additionally, nitrogen and steam were added thereto together. As a reactor, a metal tubular reactor was used. A ratio of reactants and gas hourly space velocity (GHSV) were set based on 1-butene as summarized in Table 2 below. A fixed bed reactor was filled with the prepared catalyst and the volume of a catalyst layer which the reactants contact was fixed to 20 cc. A reaction apparatus was designed such that water was injected by a vaporizer and vaporized as steam at 150° C. to be mixed along with 1-butene and oxygen and be introduced into the reactor. The amount of butene was controlled by means of a mass flow controller for a liquid, the amounts of oxygen and nitrogen were controlled by means of a mass flow controller for gas, and the amount of steam was controlled by adjusting an injection speed by means of a liquid pump. Reaction temperature was maintained at 320° C. as described in Table 2 below. After reaction, a product was analyzed using gas chromatography. Through the gas chromatography analysis, a transition rate (X), a selectivity (S_BD, S_heavy, S_COx) and a yield (Y) were measured and calculated according to Mathematical Equations 1, 2, and 3 below.

Transition rate (%)=(mol number of reacted 1-butene/mol number of supplied 1-butene)×100  [Mathematical Equation 1]

Selectivity (%)=(mol number of generated 1,3-butadiene(BD), ingredient with high boiling point (heavy), or COx/mol number of reacted 1-butene)×100  [Mathematical Equation 2]

Yield (%)=(mol number of generated 1,3-butadiene/ mol number of supplied 1-butene)×100  [Mathematical Equation 3]

As shown in Tables 1 and 2, it can be confirmed that the composite oxide catalysts for preparing butadiene according to the present disclosure (Examples 1 to 4) exhibit superior strength, and excellent butene transition rate, butadiene selectivity, and yield, compared to the composite oxide catalysts including silica as a binder (Comparative Example 1 and 3). In addition, it can be confirmed that, in the composite oxide catalysts for preparing butadiene according to the present disclosure (Examples 1 to 4), generation of ingredients with a high boiling point is greatly decreased.

In addition, it can be confirmed that the composite oxide catalyst for preparing butadiene (Examples 1 to 4) according to the present disclosure exhibit superior butene transition rate and yield, and excellent catalyst strength, compared to the composite oxide catalyst (Comparative Example 2) not including AlPO$_4$ and a binder.

Concomitantly, it can be confirmed through the results of Comparative Examples 1 and 3 that, when the amount of silica as a binder is increased, catalyst strength is increased, but butadiene selectivity, and a yield are decreased, and generation of ingredients with a high boiling point is greatly increased.

What is claimed is:

1. A composite oxide catalyst for preparing butadiene, comprising a metal composite oxide and AlPO$_4$, wherein:
   the metal composite oxide has a mole ratio of metal ingredients of Formula 1:

$Mo_{12}Bi_1Fe_cCo_5Cs_{0.01}$  [Formula 1]

where c is 1.2 to 1.3;
   the AlPO$_4$ is present in an amount of 5 to 30% by weight based on 100% by weight of the composite oxide catalyst;
   a mole ratio of Mo metal to Al metal is 12:0.5 to 3; and
   the composite oxide catalyst has a strength of 6.0 kgf or more.

TABLE 2

| | GHSV (h-1) | Temp (° C.) | P | OBR | SBR | NBR | X | S_BD | Y | S_heavy | S_COx |
|---|---|---|---|---|---|---|---|---|---|---|---|
| Comparative Example 1 | 100 | 320 | 12 | 1 | 4 | 12 | 97.69 | 93.70 | 91.53 | 1.31 | 1.28 |
| Comparative Example 2 | 100 | 320 | 12 | 1 | 4 | 12 | 96.69 | 94.91 | 91.77 | 0.61 | 0.83 |
| Example 1 | 120 | 320 | 12 | 1 | 4 | 12 | 94.95 | 95.32 | 90.50 | 0.44 | 0.71 |
| | 100 | 320 | 12 | 1 | 4 | 12 | 99.30 | 94.25 | 93.57 | 0.62 | 1.58 |
| | 120 | 320 | 12 | 1 | 4 | 12 | 98.75 | 94.72 | 93.54 | 0.41 | 1.48 |
| Comparative Example 3 | 100 | 320 | 12 | 1 | 4 | 12 | 97.16 | 92.49 | 89.90 | 1.06 | 2.26 |
| | 250 | 320 | 12 | 1 | 4 | 12 | 82.05 | 95.23 | 78.1 | 1.03 | 1.29 |
| Example 2 | 100 | 320 | 12 | 1 | 4 | 12 | 98.04 | 94.19 | 92.34 | 0.97 | 1.90 |
| | 250 | 320 | 12 | 1 | 4 | 12 | 86.49 | 95.40 | 82.42 | 0.86 | 1.22 |
| Example 3 | 100 | 320 | 12 | 1 | 4 | 12 | 97.60 | 93.49 | 91.24 | 1.06 | 2.31 |
| | 250 | 320 | 12 | 1 | 4 | 12 | 87.37 | 94.96 | 82.97 | 0.88 | 1.48 |
| Example 4 | 100 | 320 | 12 | 1 | 4 | 12 | 98.5 | 93.47 | 92.07 | 1.08 | 1.92 |
| | 250 | 320 | 12 | 1 | 4 | 12 | 88.38 | 94.36 | 83.39 | 1.01 | 1.71 |

2. The composite oxide catalyst according to claim 1, wherein a ratio of acid sites in the composite oxide catalyst is respectively 10 to 30%, 20 to 50%, and 40 to 60% based on ammonia desorption temperatures of 150° C., 580° C., and 720° C.

3. A composite oxide catalyst for preparing butadiene, comprising a metal composite oxide and a binder, wherein:
   the binder is $AlPO_4$;
   the metal composite oxide has a mole ratio of metal ingredients of Formula 1:

$$Mo_{12}Bi_1Fe_cCo_5Cs_{0.01} \quad \text{[Formula 1]}$$

where c is 1.2 to 1.3;
   the $AlPO_4$ is present in an amount of 5 to 30% by weight based on 100% by weight of the composite oxide catalyst;
   a mole ratio of Mo metal to Al metal is 12:0.5 to 3; and
   the composite oxide catalyst has a strength of 6.0 kgf or more.

4. The composite oxide catalyst according to claim 3, wherein a ratio of acid sites in the composite oxide catalyst is respectively 10 to 30%, 20 to 50%, and 40 to 60% based on ammonia desorption temperatures of 150° C., 580° C., and 720° C.

5. A method of preparing a metal composite oxide catalyst for preparing butadiene, the method comprising:
   mixing a metal composite oxide catalyst precursor powder with from 5 to 30 parts by weight $AlPO_4$ and an aqueous alcohol to form a mixture;
   kneading the mixture until a water content is about 15% by weight to form a dough;
   feeding the dough through an extruder to form an extrusion molding in a pellet; and
   firing the pellet.

6. The method of claim 5, wherein the aqueous alcohol used to form the mixture contains an equal amount of water and alcohol.

* * * * *